(12) United States Patent
Endo et al.

(10) Patent No.: US 8,485,663 B2
(45) Date of Patent: Jul. 16, 2013

(54) OPHTHALMIC APPARATUS

(75) Inventors: Masakazu Endo, Aichi (JP); Noriji Kawai, Aichi (JP)

(73) Assignee: Nidek Co., Ltd., Aichi (JP)

( * ) Notice: Subject to any disclaimer, the term of this patent is extended or adjusted under 35 U.S.C. 154(b) by 192 days.

(21) Appl. No.: 13/095,165

(22) Filed: Apr. 27, 2011

(65) Prior Publication Data

US 2011/0267582 A1    Nov. 3, 2011

(30) Foreign Application Priority Data

Apr. 30, 2010 (JP) ................................. 2010-105510

(51) Int. Cl.
*A61B 3/10* (2006.01)
(52) U.S. Cl.
USPC ........................................ 351/212; 351/221
(58) Field of Classification Search
USPC ........................................ 351/212, 211, 221
See application file for complete search history.

(56) References Cited

U.S. PATENT DOCUMENTS

| | | | |
|---|---|---|---|
| 5,684,562 A | 11/1997 | Fujieda | |
| 7,111,938 B2 | 9/2006 | Andino et al. | |
| 7,258,444 B2 * | 8/2007 | Gorin | 351/221 |
| 7,762,667 B2 | 7/2010 | Andino et al. | |
| 7,775,663 B2 | 8/2010 | Andino et al. | |
| 7,780,293 B2 | 8/2010 | Andino et al. | |
| 2004/0246440 A1 | 12/2004 | Andino et al. | |
| 2005/0225724 A1 * | 10/2005 | Klyce et al. | 351/212 |
| 2006/0274261 A1 | 12/2006 | Andino et al. | |
| 2006/0274262 A1 | 12/2006 | Andino et al. | |
| 2006/0274268 A1 | 12/2006 | Andino et al. | |
| 2010/0281021 A1 | 11/2010 | Weeber et al. | |

FOREIGN PATENT DOCUMENTS

| | | |
|---|---|---|
| JP | 06046998 A | 2/1994 |
| JP | 2005160694 A | 6/2005 |
| WO | 02088830 A1 | 11/2002 |
| WO | 2006047698 A1 | 5/2006 |

OTHER PUBLICATIONS

Extended European Search Report 11164107.2-2319 dated Jul. 29, 2011.
European Office Action issued in corresponding European Application No. 11164107.2, dated Mar. 20, 2013.

* cited by examiner

*Primary Examiner* — Hung Dang
(74) *Attorney, Agent, or Firm* — Lowe Hauptman Ham & Berner, LLP

(57) ABSTRACT

An ophthalmic apparatus includes an imaging optical system for imaging an anterior segment image including a pupil of an examinee's eye, a pupil detection unit for detecting a size of the pupil of the examinee's eye based on the imaged result by the imaging optical system, and an output unit configured to obtain size information of a far vision zone and a near vision zone for a multifocal intraocular lens and output the obtained size information and the size of the pupil detected by the pupil detection unit to be comparable. Accordingly, applicability of the multifocal intraocular lens can be determined accurately and easily.

15 Claims, 5 Drawing Sheets

OPHTHALMIC APPARATUS

CROSS-REFERENCE TO RELATED APPLICATION

This application is based on Japanese Patent Application No. 2010405510 filed with the Japan Patent Office on Apr. 30, 2010, the entire content of which is hereby incorporated by reference.

BACKGROUND

1. Technical Field

An aspect of the invention relates to an ophthalmic apparatus that measures a pupil size of an examinee's eye.

2. Related Art

As an apparatus for measuring a pupil size of an examinee's eye, one that images an anterior segment image including the pupil of the examinee's eye and measures the pupil size by use of a profile of an iris on the imaged image is known (refer to JP-A-6-46998).

SUMMARY

In recent years, a multifocal intraocular lens for both far vision and near vision has been known. However, such a multifocal intraocular lens has different near vision zone (near zone) and far vision zone (distance zone) depending on attributes of the lens (a manufacturer, a product name, and the like). Accordingly, some lenses may not be able to provide a favorable prescription result depending on the size of the pupil of the examinee's eye.

A technical object in one aspect of the invention is to provide an ophthalmic apparatus that can check applicability of a multifocal intraocular lens easily.

One aspect of the invention includes the following configuration. An ophthalmic apparatus of one aspect of the invention includes: an infrared light source for irradiating an examinee's eye with infrared light; an imaging optical system for imaging an anterior segment image including a pupil of the examinee's eye; a computing part configured to detect an edge of the pupil by image processing from the anterior segment image irradiated with the infrared light obtained by the imaging optical system, and derive pupil information including a pupil diameter of the examinee's eye based on the detected result; a memory part configured to store per multifocal intraocular lens size information of zones in a plurality of different multifocal intraocular lenses that have a far vision zone and a near vision zone; and an output part for outputting the pupil information derived by the computing part and the size information stored in the memory part to be comparable.

According to one embodiment of the invention, applicability of a multifocal intraocular lens can be checked easily.

BRIEF DESCRIPTION OF THE DRAWINGS

The foregoing and other objects, features, aspects and advantages of the invention will become more apparent from the following detailed description when taken in conjunction with the accompanying drawings, in which.

DESCRIPTION OF EMBODIMENTS

Figure 1:
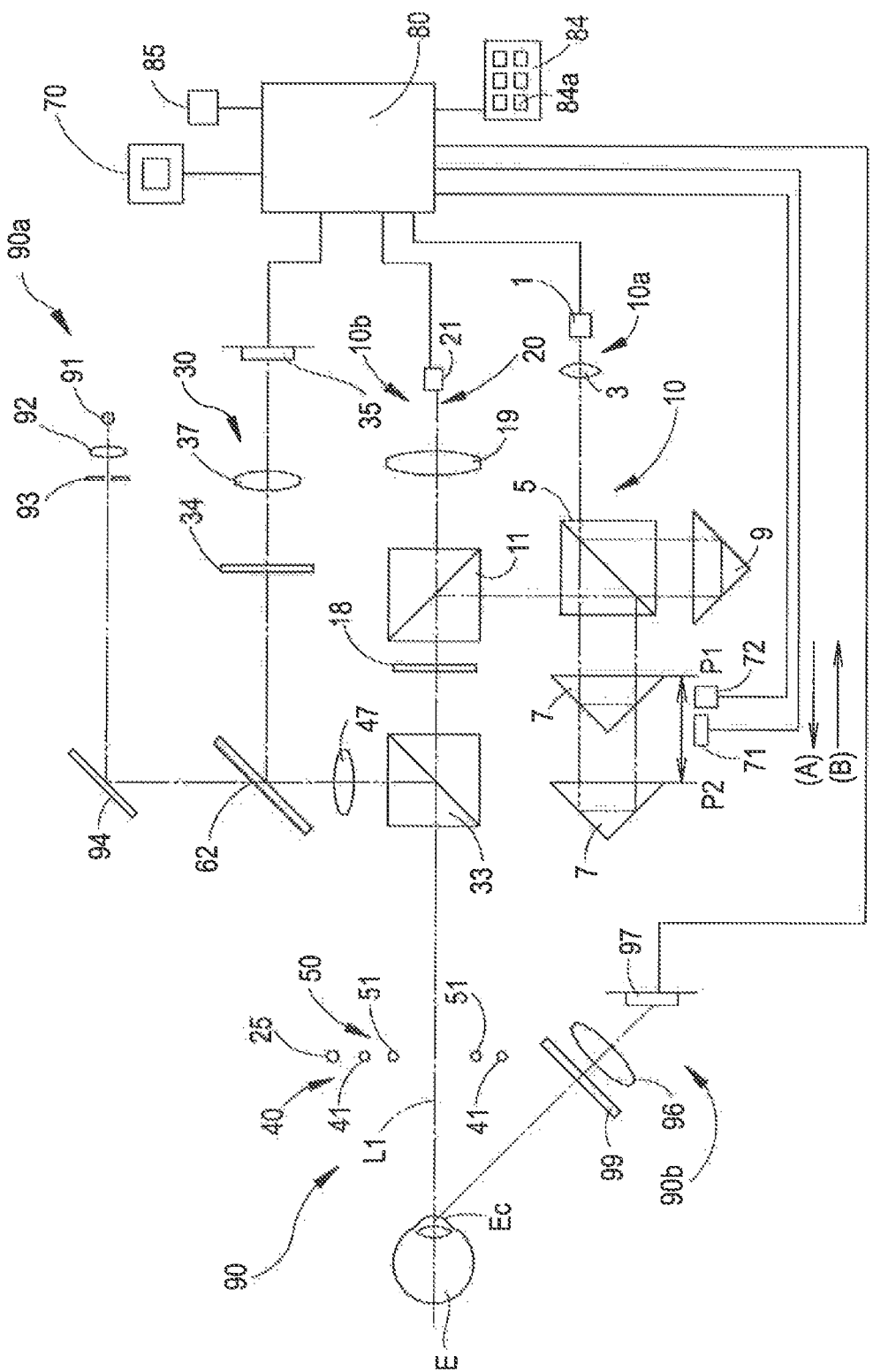
FIG. 1 illustrates a schematic configuration of an optical system of an ophthalmic apparatus according to an embodiment of the invention.

Preferred embodiments of the invention will be described below with reference to the accompanying drawings, in which like reference characters designate similar or identical parts throughout the several views thereof.

An embodiment according to an aspect of the invention will be described below based on the drawings. FIG. 1 illustrates a schematic configuration of an optical system of an ophthalmic apparatus according to an embodiment of the invention. The optical system is broadly classified into an ocular axial length measuring optical system (measuring unit) 10, a kerato-projecting optical system 40, an alignment projecting optical system 50, an anterior segment front surface imaging optical system 30, and an anterior segment cross-sectional image imaging optical system 90. The kerato-projecting optical system 40 projects a target for measuring the shape of the cornea onto the cornea of an examinee's eye. The anterior segment front surface imaging optical system 30 images an anterior segment front surface image. The anterior segment cross-sectional image imaging optical system 90 images an anterior segment cross-sectional image of the examinee's eye. These optical systems are built into a casing that is not illustrated. The casing is driven by a well-known alignment shifting mechanism via an operation member (for example, a joystick). Thereby, the casing is moved in three dimensions with respect to the examinee's eye.

The projecting optical system 40 has a ring-shaped light source 41 disposed with a measurement optical axis L1 as the center. The projecting optical system 40 is used for measuring the shape of the cornea (curvature, astigmatic axial angle, and the like) by projecting a ring target on the cornea of the examinee's eye. As the light source 41, for example, an LED that generates infrared light or visible light is used. The light source of the projecting optical system 40 only needs to have at least three or more point light sources that are arranged on the same circle centered on the optical axis Thus, the light source may be an intermittent ring light source. Further, the projecting optical system 40 may be a placido target projecting optical system that projects a plurality of ring targets.

The alignment projecting optical system 50 has a projection light source 51 that generates infrared light (for example, λ=970 nm) and is disposed inside the light source 41. The light source 51 is used for projecting an alignment target on the cornea of the examinee's eye. The alignment target projected on the cornea is used for alignment with respect to the examinee's eye (for example, auto-alignment, alignment detection, manual alignment, and the like). In the embodiment, the projecting optical system 50 is an optical system that projects a ring target on the cornea of the examinee's eye. The ring target is also used as a Mayer ring. The light source 51 of the projecting optical system 50 is also used as an anterior segment light for illuminating the anterior segment by infrared light from a diagonal direction. An optical system that projects parallel light on the cornea may be further provided to the projecting optical system 50. In this configuration, alignment can also be carried out in the front-rear direction by combining the parallel light with finite light from the projecting optical system 50.

The anterior segment front surface imaging optical system 30 is used for imaging an anterior segment front surface image of the examinee's eye. The anterior segment front surface imaging optical system 30 has a dichroic mirror 33, an objective lens 47, a dichroic mirror 62, a filter 34, an imaging lens 37, and a two-dimensional imaging device 35.

Anterior segment reflection light, which is obtained when light from the projecting optical system 40 and the projecting optical system 50 described above is reflected at the anterior segment, is formed into an image on the two-dimensional imaging device 35 via the dichroic mirror 33, the objective lens 47, the dichroic mirror 62, the filter 34, and the imaging lens 37.

The ocular axial length measuring optical system 10 has a light projecting optical system 10a and a light receiving optical system 10b. The light projecting optical system 10a includes a measurement light source 1, a collimator lens 3, a beam splitter 5, a first triangular prism (corner cube) 7, a second triangular prism 9, a polarizing beam splitter 11, and a quarter wavelength plate 18. The measurement light source 1 is a light source that emits low coherent light (in the embodiment, it is also a fixation lamp). The collimator lens 3 makes a light flux emitted from the measurement light source 1 into a parallel light flux. The beam splitter 5 splits light emitted from the light source 1. The first triangular prism (corner cube) 7 is disposed in the transmission direction of the beam splitter 5. The second triangular prism 9 is disposed in the reflection direction of the beam splitter 5.

Light (linearly polarized light) emitted from the light source 1 is collimated by the collimator lens 3, and then split by the beam splitter 5 into a first measurement light (reference light) and a second measurement light. The first measurement light is reflected by the triangular prism 7 and bent back. Meanwhile, the second measurement light is reflected by the triangular prism 9 and bent back. Subsequently, the first measurement light and the second measurement light are combined by the beam splitter 5. The combined light is reflected by the polarizing beam splitter 11, and then converted to circularly polarized light by the quarter wavelength plate 18. Then, at least the cornea and fundus of the examinee's eye are irradiated with the circularly polarized light via the dichroic mirror 33. At this time, when the measurement light flux including the circularly polarized light is reflected at the cornea and fundus of the examinee's eye, the phase of the light flux is displaced by ½ a wavelength.

The light receiving optical system 10b is disposed for receiving light (interference light) obtained by the interference of cornea reflection light, which is obtained when measurement light irradiated by the light projecting optical system 10a is reflected at the cornea, and fundus reflection light, which is obtained when measurement light is reflected at the fundus. The light receiving optical system 10b includes the dichroic mirror 33, the quarter wavelength plate 18, the polarizing beam splitter 11, a condenser lens 19, and a light receiving device 21.

The cornea reflection light and the fundus reflection light pass through the dichroic mirror 33, and then are converted to linearly polarized light by the quarter wavelength plate 18. Subsequently, the both reflection lights having passed through the polarizing beam splitter 11 are condensed by the condenser lens 19 and then received by the light receiving device 21.

The triangular prism 7 is used as an optical-path-length changing member for changing the optical path length. The triangular prism 7 is moved linearly relative to the beam splitter 5 along the optical axis direction by the driving of a driving part 71 (for example, a motor). The optical-path-length changing member may also be a triangular mirror. The position of the prism 7 during driving is detected by a position detecting sensor 72 (a potentiometer, an encoder, and the like).

In the above explanation, a configuration in which the cornea reflection light and the fundus reflection light are made to interfere has been described. However, this configuration is not absolutely necessary. In other words, the ophthalmic apparatus of the invention may include an optical interference optical system including a beam splitter (light splitting member) that splits light emitted from a light source, a sample arm, a reference arm, and a light receiving device that receives interference light. In this optical interference optical system, interference light obtained by the interference of measurement light with which the examinee's eye is irradiated via the sample arm and reference light from the reference arm is received by the light receiving device. In this case, the optical-path-length changing member is disposed on at least any of the sample arm and the reference arm.

In the above configuration, the optical path length of reference light is changed by linearly moving the prism 7. However, this configuration is not absolutely necessary. For example, the ophthalmic apparatus of the invention may have a configuration in which the optical path length of reference light is changed by an optical delay mechanism via a rotating reflector (for example, refer to JP-A-2005-160694).

The anterior segment cross-sectional image imaging optical system 90 includes a light projecting optical system (projecting optical system) 90a and a light receiving optical system (imaging optical system) 90b. The light projecting optical system 90a projects a slit light for forming an anterior segment cross-sectional image on an examinee's eye E. The light receiving optical system 90b receives anterior segment reflection light (anterior segment scattered light) obtained when the slit light projected by the light projecting optical system 90a is reflected at the anterior segment, and then images an anterior segment cross-sectional image.

The light projecting optical system 90a includes a light source 91, a condenser lens 92, a slit plate 93, a total reflection mirror 94, a dichroic mirror 62, the objective lens 47 and the dichroic mirror 33.

The light receiving optical system 90b includes a two-dimensional imaging device 97 and an imaging lens 96. The imaging lens 96 leads anterior segment reflection light, which is obtained when light from the light projecting optical system 90a is reflected at the anterior segment, to the imaging device 97. The light receiving optical system 90b has a configuration that images an anterior segment cross-sectional image based on the Scheimpflug principle. Basically, the light receiving optical system 90b is arranged such that its optical axis (imaging optical axis) intersects with the optical axis of the light projecting optical system 90a at a predetermined angle. The light cross-section of the projection image by the light projecting optical system 90a, the lens system (cornea and the imaging lens 96) including the cornea of the examinee's eye, and the imaging surface of the imaging device 97 are arranged such that they are in a Scheimpflug relationship. A filter 99 is disposed on the front side (the examinee's eye E side) of the lens 96. Among the light emitted from the light source 91, the filter 99 passes only light (blue light) used for imaging an anterior segment cross-sectional image.

Next, a control system will be described. A control part 80 performs control of the entire apparatus and calculation of measurement results. The control part 80 is connected to the light source 1, the light source 91, the light source 51, the light source 41, the light receiving device 21, the imaging device 35, the imaging device 97, a monitor 70, a memory 85, and the like. The control part 80 is also connected to an operation part 84 for performing various input operations. The operation part 84 is provided with a mode switching switch 84a. This mode switching switch 84a switches between a normal measurement mode for measuring the ocular axial length, the shape of the cornea, and the like and a pupil diameter measurement mode for measuring the shape of the cornea and the anterior chamber depth and calculating the actual pupil diameter by use of the measurement result, for example. Also, the operation part 84 may be a general-purpose interface such as a mouse as an operation input part or a touch panel.

The memory 85 has stored therein a software program for calculation of the ocular axial length, the shape of the cornea, and the like by the control part 80, a software program for calculation of the actual pupil diameter by the control part 80, and the like, as well as various control programs.

The apparatus measures the pupil diameter of the eye E. The apparatus then displays information for determination of whether or not an intraocular lens is applicable to the eye E by an examiner based on the measurement result (this will be described later in details). For this reason, the memory 85 has stored therein optical design (size information of a far vision zone and a near vision zone) corresponding to attributes of each multifocal intraocular lens (product information such as a manufacturer and a product name).

An optical part of the multifocal intraocular lens is designed to have a plurality of focuses such as a long distance focus and a short distance focus. The optical part of the lens is provided with at least one far vision zone and at least one near vision zone. It is to be noted that such a zone-type multifocal lens includes one having at the center a zone for both far vision and near vision containing a diffraction grating and having on the periphery a refractive near vision zone.

Here, the size information stored in the memory 85 will be described. For example, an optical part of a multifocal intraocular lens is configured to have concentric circles forming three zones. In this case, size information of an innermost near vision zone (for example, $\phi 1 \leq 2.0$ mm), size information of a transitional zone (for example, $2.0 < \phi 2 \leq 4.0$ mm), and size information of an outermost far vision zone (for example, $4.0 < \phi 3 \leq 6.0$ mm) are stored in the memory 85. It is to be noted that the above size information represents an effective area of each zone.

<Normal Measurement Mode>

The operation of the apparatus including the configuration described above will be described below. The examiner moves the apparatus in the up-down, right-left, and front-rear directions by use of a not shown operation tool such as a joystick while looking at the alignment state of the examinee's eye displayed on the monitor 70. In this manner, the examiner locates the apparatus at a predetermined position with respect to the examinee's eye E. In this case, the examiner requests the examinee such that the examinee's eye fixates a fixation target.

Figure 2:
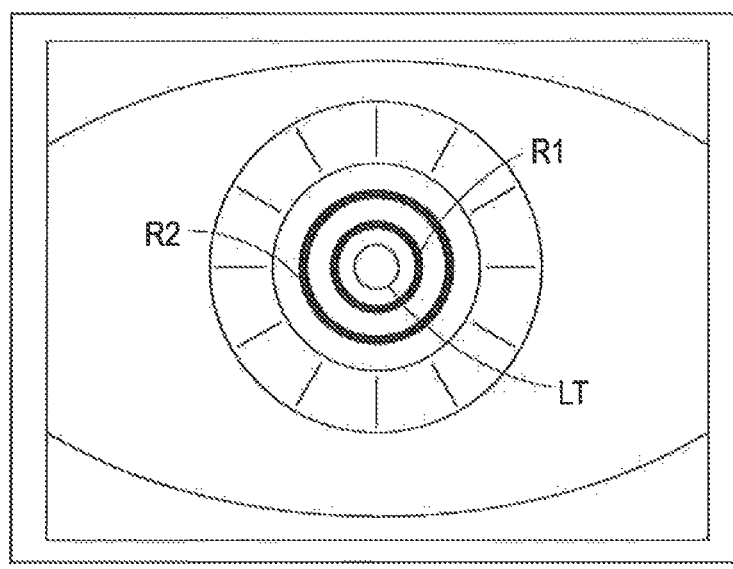
FIG. 2 illustrates an anterior segment observation screen displaying an imaged anterior segment image.

FIG. 2 illustrates an anterior segment observation screen displaying an anterior segment image imaged by the imaging device 35. During alignment, the light source 51 and the light source 41 are illuminated. The examiner carries out alignment of the apparatus in the up-down and right-left directions such that a reticle LT displayed electronically and a ring target R1 by the light source 51 may be concentric as shown in FIG. 2. The examiner also carries out alignment of the apparatus in the front-rear direction such that the ring target R1 may be in focus. On the outer side of the ring target R1, a ring target R2 by the light source 41 is displayed.

<Calculation of Ocular Axial Length>

After the alignment, a trigger signal for measurement initiation is output automatically or manually. When the measurement light source 1 is illuminated by the control part 80, the examinee's eye is irradiated with a measurement light by the ocular axial length measuring optical system 10. A reflection light obtained when the measurement light is reflected by the examinee's eye then enters the light receiving device 21 of the light receiving optical system 10b.

The control part 80 reciprocatingly moves the first triangular prism 7 by controlling the driving part 71. The control part 80 calculates the ocular axial length based on a light receiving signal output from the light receiving device 21 and the timing at which interference light is detected by the light receiving device 21.

Information that has been acquired regarding the ocular axial length of the examinee's eye is stored in the memory 85. After a predetermined number of measurements have been completed (or after a predetermined number of values of the ocular axial length of the examinee's eye have been obtained), the control part 80 ends the reciprocating movement of the prism 7 and returns the position of the prism 7 to its initial position. It is to be noted that, in the normal measurement mode, the shape of the cornea and the anterior chamber depth as well as the ocular axial length can be measured appropriately.

<Pupil Diameter Measurement Mode>

When the mode switching switch 84a is selected to switch the mode to the pupil diameter measurement mode by the examiner, the control part 80 switches the mode from the normal measurement mode to the pupil diameter measurement mode.

In the pupil diameter measurement mode, the control part 80 detects the size of the pupil of the examinee's eye based on the imaging result by the imaging optical system 30. The control part 80 then outputs the detected size of the pupil and size information for a multifocal intraocular lens in a state where they can be compared.

Also, the control part 80 corrects the detected size of the pupil. In this case, the apparatus irradiates the cornea with measurement light by the projecting optical system 40. The apparatus then receives the reflection light by the imaging device 35 and detects the shape of the cornea based on the light receiving result. Thereafter, the apparatus obtains anterior chamber depth information of the eye E by the cross-sectional image imaging optical system 90. Further, the apparatus calculates the ratio (enlargement ratio) of an apparent anterior chamber depth to an actual anterior chamber depth by use of the obtained anterior chamber depth information and the detection result of the shape of the cornea. The apparatus then corrects the detected size of the pupil into the size of the pupil in consideration of the shape of the cornea and the anterior chamber depth of the examinee's eye by use of the calculated enlargement ratio and outputs the corrected size of the pupil as a measurement result. This will be described below more specifically.

<Measurement of Cornea Curvature>

First, the shape of the cornea is measured. Alignment is carried out in a similar manner to the above, and a predetermined trigger signal is generated. In response to this, the control part 80 images an anterior segment image by use of the imaging device 35. Subsequently, the control part 80 obtains an anterior segment image including the ring targets R1 and R2 as a still image based on an imaging signal output from the imaging device 35 and stores it in the memory 85 (refer to FIG. 2).

The control part 80 then calculates the shape of the cornea of the examinee's eye (for example, cornea curvature in a strong principal meridian direction and a weak principal meridian direction, cornea astigmatic axial angle, and the like) based on the ring target R2 on the anterior segment image stored in the memory 85 and stores the calculation result in the memory 85.

<Calculation of Pupil Diameter>

Next, the control part 80 detects a pupil diameter based on the anterior segment image stored in the memory 85. Hereinafter, a method for detecting the pupil diameter by deriving an edge position of the pupil based on the anterior segment image will be described with reference to FIGS. 3A, 3B, 3C, and 3D.

Figure 3A:
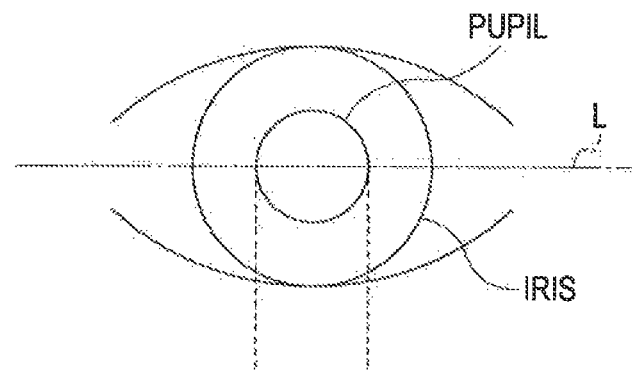
FIGS. 3A, 3B, 3C, and 3D illustrate a method for deriving a pupil edge; position.
Figure 3B:
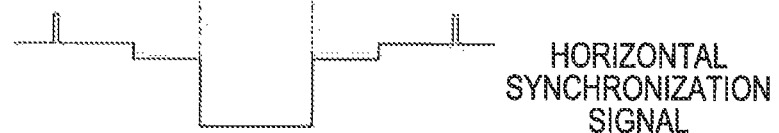
Figure 3C:
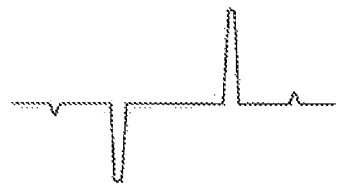
Figure 3D:
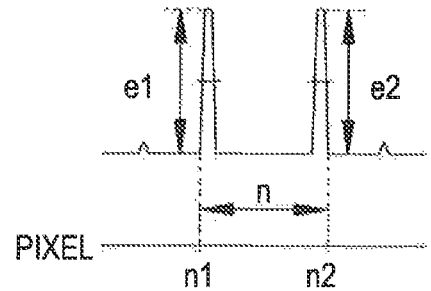

FIG. 3A illustrates a pupil image state stored in the memory 85. FIG. 3B illustrates an image signal on a scanning line L. To find a border (edge) between the pupil (dark part) and the iris (bright part), the signal waveform shown in FIG. 3B is first differentiated. A signal waveform obtained by this differentiation is one shown in FIG. 3C. This signal has positive and negative numbers. This is further squared to obtain a signal having positive numbers as shown in FIG. 3D. In the signal shown in FIG. 3D, edges of a first peak having a height e1 and a last peak having a height e2 are defined as positions of pixels corresponding to heights that are ½ of the heights (amplitude) of the peaks, for example. In this case, pixel positions n1 and n2 are coordinate positions of the edges on the scanning line L.

Also, from the pixel positions n1 and n2, a number n of pixels existing between them is derived. When a length of one pixel is K, and an optical magnification is P, a distance between the pixel positions n1 and n2 (pupil diameter PS') is derived from the following equation:

$$PS' = n \times K/P.$$

The values K and P are known values unique to the apparatus. Accordingly, the pupil diameter is derived by deriving the above pixel number n.

At this time, a position of a pupil center is detected based on positional information of a pupil profile. The pupil diameters in the meridian directions are calculated with reference to the pupil center. It is to be noted that, in imaging of the anterior segment image used for detection of the pupil diameter, both or either the pupil in a bright-field state and/or the pupil in a dark-field state may be imaged. That is, in detection of the pupil diameter, both or either the size of the pupil in the bright-field state and/or the size of the pupil in the dark-field state may be detected. In the ease of detecting the size of the pupil in the bright-field state, the control part 80 illuminates a visible light source 25 for irradiating the examinee's eye with visible light and irradiates the examinee's eye with the visible light from the visible light source 25. Irradiation with the visible light constricts the pupil to enable imaging in the bright-field state. In this manner, the control part 80 obtains the anterior segment image irradiated with the visible light and calculates the pupil diameter in the bright-field state from this image. On the other hand, the pupil diameter of the examinee's eye in the dark-field state is calculated by use of infrared light illumination.

A part of the anterior segment image displayed on the monitor 70 as described above passes not only through the imaging optical system 30 but also through the interior of the eyeball (anterior segment light transmitting part) and the cornea. Thus, the anterior segment image is influenced by distortion by refraction at the interior of the eyeball and the cornea. Accordingly, the anterior segment image displayed on the monitor 70 is an apparent image after refraction. The pupil diameter calculated from the anterior segment image displayed on the monitor 70 is an apparent value. In other words, to calculate the actual pupil diameter (hereinafter referred to as actual pupil diameter), the influence of the anterior segment light transmitting part and the cornea residing therebetween needs to be considered (this will be described later in details).

<Calculation of Anterior Chamber Depth>

Next, the anterior chamber depth of the examinee's eye is detected. First, the anterior segment cross-sectional image is imaged. When alignment with respect to the eye E is carried out, and a trigger signal is generated, the control part 80 illuminates the light source 91. Light from the light source 91 is condensed by the condenser lens 92, and then passes through the slit plate 93 to become a slit light. The slit light is reflected at the total reflection mirror 94, passes through the dichroic mirror 62, passes through the objective lens 47, and is reflected at the dichroic mirror 33. The slit light is then condensed on the anterior segment to form a slit cross-sectional image (anterior segment cross-sectional image) on the anterior segment. The anterior segment cross-sectional image is imaged by the imaging device 97 via the filter 99 and the lens 96. The control part 80 then analyzes data of the anterior segment cross-sectional image obtained by the imaging device 97 to calculate the anterior chamber depth at the anterior segment. In the case of calculating the anterior chamber depth, a distance from the cornea to an anterior surface of a crystalline lens has only to be measured. That is, the distance may be a distance from a cornea anterior surface or a distance from a cornea posterior surface.

Figure 4:
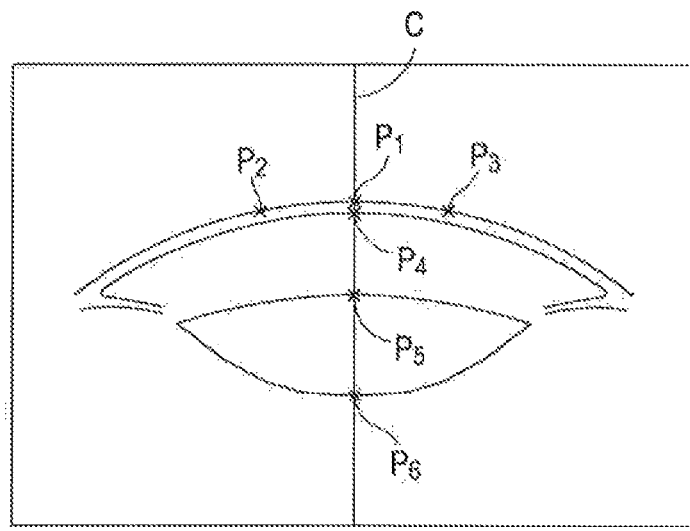
FIG. 4 illustrates determination of a measurement axis on an imaged cross-sectional image.

FIG. 4 illustrates an imaged anterior segment cross-sectional image. Based on this cross-sectional image, a measurement axis C for measuring the shape of the anterior segment such as the anterior chamber depth is determined. The control part 80 first detects three points (P1, P2, and P3) along the cornea anterior surface based on a concentration value (luminance value) on each layer in the imaged image. The control part 80 makes circle approximation of the cornea anterior surface based on these three points to obtain a circle corresponding to the cornea anterior surface. The control part 80 then regards a line along the curvature center of this circle as the measurement axis C and draws the measurement axis C on the image. Subsequently, the control part 80 detects a cross point P4 of the measurement axis C with the cornea posterior surface, a cross point P5 of the measurement axis C with the anterior surface of the crystalline lens, and a cross point P6 of the measurement axis C with a posterior surface of the crystalline lens based on a concentration value (luminance value) on each layer in the imaged image. The control part 80 then calculates a distance from the point P1 to the point P5 and regards this distance as the anterior chamber depth.

A part of the anterior segment cross-sectional image displayed on the monitor 70 as described above passes not only through the light receiving optical system 90b but also through the interior of the eyeball (anterior segment light transmitting part) and the cornea. Thus, the anterior segment cross-sectional image is influenced by distortion by refraction at the interior of the eyeball and the cornea. Accordingly, the anterior segment cross-sectional image displayed on the monitor 70 is an apparent image after refraction. The pupil diameter calculated from the image is an apparent value.

<Calculation of Corrected Value for Pupil Diameter>

Next, the control part 80 calculates the actual pupil diameter based on the measurement result obtained as above. Specifically, the control part 80 calculates an actual pupil diameter PS by use of an apparent pupil diameter PS'. To do so, the control part 80 first calculates a ratio (enlargement ratio) M of an apparent anterior chamber depth ACD' to an actual anterior chamber depth ACD from the apparent and actual ones. The control part 80 then applies the enlargement ratio M to the apparent pupil diameter PS' to enable calculation of the actual pupil diameter PS.

Figure 5:
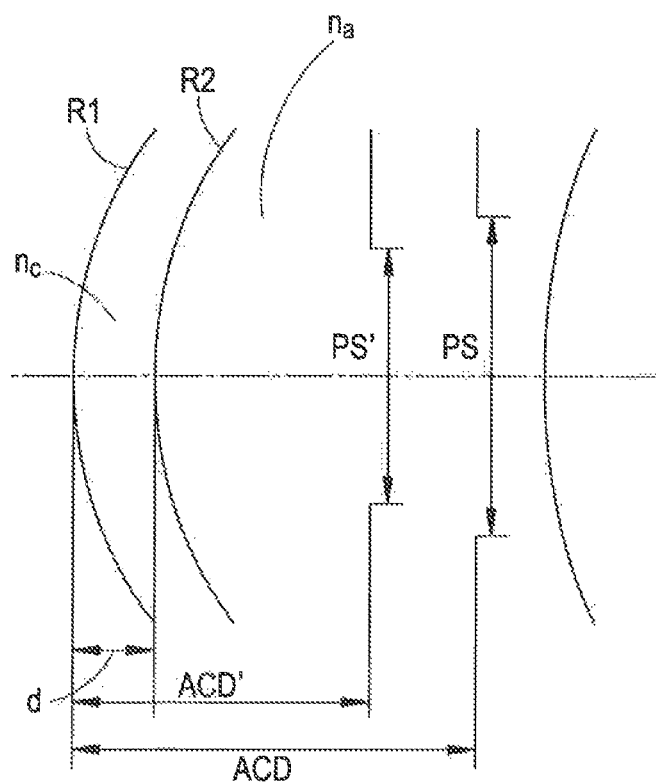
FIG. 5 illustrates a method for deriving an actual pupil diameter.

The apparent anterior chamber depth is corrected to calculate the actual anterior chamber depth. This calculation procedure will be described below more specifically with reference to FIG. 5.

In the following description, apparent pupil diameter=PS', actual pupil diameter=PS, apparent anterior chamber depth=ACD', actual anterior chamber depth=ACD, enlargement ratio=M, refractive power of the entire cornea=$\phi$, refractive power of the cornea anterior surface=$\phi a$, refractive power of the cornea posterior surface=$\phi p$, cornea thickness=d, cornea anterior surface curvature=R1, cornea posterior surface curvature=R2, cornea refraction index=nc, and anterior chamber refraction index=na. It is to be noted that the refraction index in the atmosphere is 1.

First, refractive power of each border surface of the examinee's eye is calculated. The refractive power of the cornea anterior surface is $$\phi a=(nc-1)/R1.$$

The refractive power of the cornea posterior surface is $$\phi p=(na-nc)/R2.$$

The refractive power of the entire cornea is $$\phi=\phi a+\phi p-(d\times\phi a\times\phi p/nc).$$

Thus, the actual anterior chamber depth ACD is calculated by use of the apparent anterior chamber depth ACD' by $$ACD=(1/ACD'-\phi)^{-1}na.$$

In this case, a principal point position of the entire cornea is approximately the cornea anterior surface position. Accordingly, the principal point position is treated as the cornea anterior surface position.

Next, the enlargement ratio M is calculated from the apparent anterior chamber depth ACD' and the actual anterior chamber depth ACD. Here, the apparent anterior chamber depth ACD' is derived without considering the refraction index of the actual medium (with the refraction index being 1). The actual anterior chamber depth ACD in the examinee's eye is derived in consideration of the refraction index of the actual medium. That is, in paraxial calculation, a reduced distance S/n, made by reducing a distance S in a medium having the refraction index of n to a medium having the refraction index of 1, is used. The enlargement ratio M, which is the ratio of the apparent anterior chamber depth to the actual anterior chamber depth, is $$M=(ACD'/1)/(ACD/na).$$

Consequently, the actual pupil diameter PS is calculated by use of the apparent pupil diameter PS' by $$PS=PS'/M.$$

The actual pupil diameter can be calculated from the apparent pupil diameter in the above manner. Accordingly, the size of the pupil of the examinee's eye can be measured accurately.

<Determination of Multifocal IOL by Use of Pupil Diameter>

First, determination of applicability of an IOL by use of the pupil diameter will be described briefly. The control part 80 obtains size information of a far vision zone and a near vision zone in a multifocal intraocular lens. The control part 80 then outputs the size of the pupil of the examinee's eye and the size information on the monitor 70 in a state where they can be compared based on the obtained size information and the imaging result obtained by the imaging optical system 30 (refer to FIG. 6).

Preferably, the control part 80 controls the monitor 70 to form a graphic (106) that changes in accordance with the detected size of the pupil and outputs it as pupil information of the examinee's eye. The control part 80 also forms graphics (107 (111, 112, 113)) that change in accordance with the sizes of the far vision zone and the near vision zone and outputs it together with the pupil information of the examinee's eye.

Figure 6:
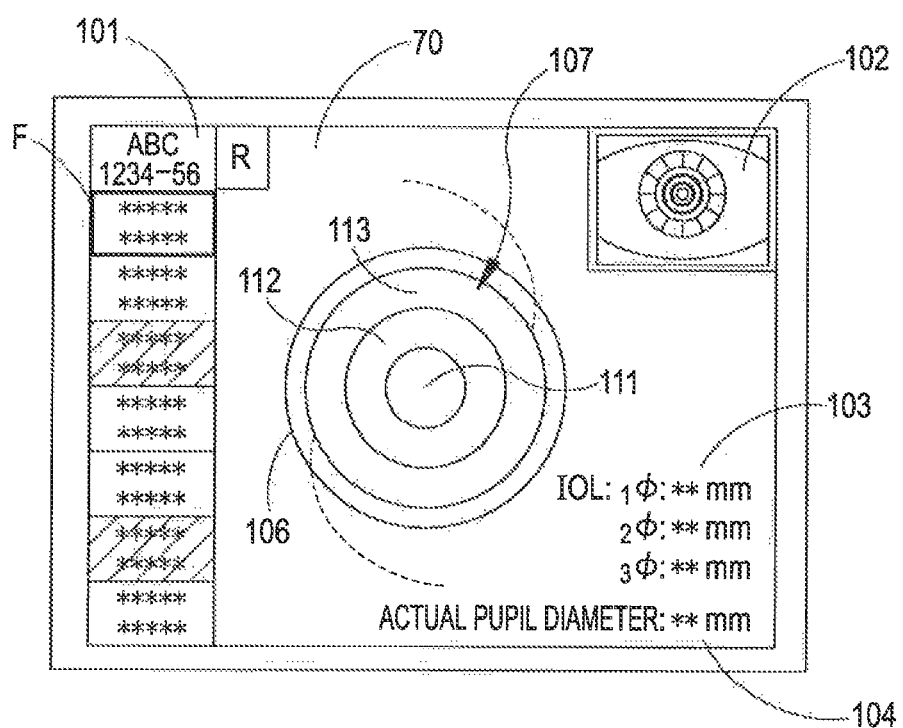
FIG. 6 illustrates a screen on which a first graphic based on a pupil diameter and a second graphic representing optical design for an intraocular lens are displayed to overlap.

The specific example will be described below. As shown in FIG. 6, the control part 80 electronically displays a first graphic 106 representing the size of the actual pupil diameter PS on the monitor 70 based on the actual pupil diameter PS calculated in the pupil diameter measurement mode. The first graphic 106 is displayed as a circle drawn in solid line, for example. Also, the display size can be changed to correspond to the size of the actual pupil diameter PS. More specifically, in a case where the display magnification is set to 8.5 times, and where the actual pupil diameter PS is 4 mm, a circle having a diameter of 34 mm is displayed on the monitor 70 as the first graphic 106. The calculation result may be typed out. Two first graphics 106 corresponding to the sizes of the pupil in the bright-field state and in the dark-field state may be output, respectively. Also, the control part 80 displays an intraocular lens list 101 on the left position of the screen on the monitor 70. The intraocular lens list 101 shows intraocular lenses to be determined together with their attributes (a manufacturer, a product name, and the like). The examiner selects an intraocular lens that he/she desires to determine by use of this list.

When an intraocular lens is selected by the examiner, the control part 80 retrieves optical design (size information of a far vision zone and a near vision zone) for the selected intraocular lens from the memory 85. The control part 80 then electronically displays the retrieved optical design on the monitor 70 as a second graphic 107. The second graphic 107 is displayed as a graphic that schematically shows the intraocular lens, for example. Also, the display size can be changed to correspond to the optical design.

In the illustrative display of the second graphic 107, the control part 80 displays a graphic 111 corresponding to size information of an innermost near vision zone, a graphic 112 corresponding to size information of a transitional zone, and a graphic 113 corresponding to size information of an outermost far vision zone in dotted line based on the optical design for the selected multifocal intraocular lens.

The first graphic 106 and the second graphic 107 are displayed at the same magnification such that the actual pupil diameter and the optical design can be compared. Also, the first graphic 106 and the second graphic 107 are displayed to overlap such that their centers may correspond.

Also, on the monitor 70, an anterior segment image 102 obtained as above is displayed. Also, on the monitor 70, values 103 representing the optical design (size information of the far vision zone and the near vision zone) for the specified intraocular lens and a measurement value 104 of the actual pupil diameter PS are displayed. For example, in a case where the optical part of the multifocal intraocular lens is configured to have concentric circles forming three zones, the size information at the areas is displayed as values ($\phi 1$, $\phi 2$, and $\phi 3$).

Also, the examiner can select an intraocular lens to be determined by moving a frame F displayed to be superimposed on the intraocular lens list 101. The control part 80 then retrieves optical design for the selected intraocular lens from the memory 85 and displays the corresponding second graphic 107.

Hence, the examiner looks at the monitor 70 to compare the first graphic 106 with the second graphic 107 and compare the values 103 with the measurement value 104. Thus, the examiner can easily check whether or not the effective area of each intraocular lens falls within the actual pupil diameter of the eye E.

<Description of Multifocal Lens>

The invention is also useful for determination of applicability of a multifocal intraocular lens. The multifocal intraocular lens is designed to have a plurality of focuses such as a long distance focus, an intermediate distance focus, and a short distance focus. In the multifocal intraocular lens, even small misalignment between the pupil center and the lens center will have a great effect on the vision. Accordingly, the correction range of the multifocal intraocular lens preferably falls within the pupil accurately. In one example, the multifocal intraocular lens is configured to have concentric circles forming three zones, and two of these zones preferably fall within the pupil diameter, in this case, since the inter-zone distance is small, even small misalignment will cause the two zones not to fall within the pupil diameter. This may have an effect on the vision.

More specifically, in a case of using a refractive multifocal lens, the near vision may not be corrected sufficiently if the pupil diameter is not 4.5 mm or longer. Accordingly, it is preferable to determine whether or not the correction range of the intraocular lens falls within the pupil diameter accurately by comparison of the size information for the intraocular lens with the pupil diameter. It is also preferable to measure the size of the pupil diameter accurately. In terms of this, the above method enables accurate measurement of the size of the pupil of the examinee's eye. Accordingly, applicability of the multifocal intraocular lens can be determined appropriately.

Meanwhile, in the embodiment, the examiner determines applicability of the intraocular lens. However, the control part 80 may determine applicability of the intraocular lens. In this case, the control part 80 determines whether or not the effective areas of the far vision zone and the near vision zone set per intraocular lens fall within the calculated actual pupil diameter. When the control part 80 ends the determination of applicability of each intraocular lens, the control part 80 displays the result on the intraocular lens list 101 such that the examiner can recognize it.

Specifically, the control part 80 hatches a portion corresponding to an applicable intraocular lens on the intraocular lens list 101 in FIG. 6. This enables the examiner to recognize that an unhatched portion is out of the applicable range. Meanwhile, in the embodiment, the applicable intraocular lens can be recognized depending on whether or not it is hatched. However, the embodiment is not limited to this configuration, and any display manner may be used as long as applicability of the intraocular lens can be recognized. For example, a display color of a portion corresponding to an applicable intraocular lens may differ from those of the other portions to enable recognition of the applicable intraocular lens.

Meanwhile, in the embodiment, a circle is formed based on the actual pupil diameter and is displayed at a predetermined display magnification. However, the embodiment is not limited to this configuration. For example, edges of the pupil may be detected, and the detected pupil shape may be displayed at a predetermined display magnification.

Meanwhile, in the embodiment, the graphics formed based on the pupil diameter and the optical design for the intraocular lens are displayed on the monitor 70. However, the embodiment is not limited to this configuration. For example, an anterior segment image imaged by the imaging optical system 30 may be output as pupil information of the examinee's eye, and a graphic representing the optical design may be displayed to be superimposed onto this anterior segment image. In this case, the anterior segment image and the graphic display are set to have the same display magnification.

More specifically, when the graphic representing the optical design is to be displayed, its display magnification is set to be the same as that of the anterior segment image. Here, the pupil displayed on the anterior segment image is an apparent pupil. Thus, the graphic representing the optical design is displayed at an apparent magnification. That is, the graphic representing the optical design is changed by use of the enlargement ratio M calculated from the apparent anterior chamber depth and the actual anterior chamber depth. Subsequently, the changed graphic is displayed to be superimposed onto the anterior segment image.

Also, the graphic representing the actual pupil diameter and the graphic representing the optical design for the intraocular lens may be combined and displayed on the anterior segment image.

Meanwhile, in the embodiment, to calculate the anterior chamber depth, the anterior segment cross-sectional image imaging apparatus that projects the slit light on the examinee's eye E and images the anterior segment cross-sectional image is used. However, the embodiment is not limited to this configuration. For example, in calculation of the anterior chamber depth, an optical interference type measurement apparatus (for example, the aforementioned ocular axial length measuring optical system 10 or an anterior segment OCT) or an ultrasonic measurement apparatus that obtains the anterior chamber depth by ultrasound waves may be used.

The optical interference type measurement apparatus or the ultrasonic measurement apparatus is an apparatus for measuring an actual anterior chamber depth. Thus, the apparent anterior chamber depth and the enlargement ratio M are calculated by use of the aforementioned equations, and the actual pupil diameter PS is calculated based on these.

Also, the kerato-projecting optical system does not need to be used to measure the shape of the cornea. For example, the anterior chamber depth and the shape of the cornea may be detected by use of the aforementioned Scheimpflug camera.

Also, the apparatus does not need to mount the anterior segment cross-sectional image imaging apparatus integrally. The apparatus may be configured to use an anterior chamber depth measured separately (the same is true of the measurement result of the shape of the cornea).

Meanwhile, the method in the embodiment is applicable to other ophthalmic apparatuses that image an anterior segment image and measure a pupil diameter. For example, the method in the embodiment is applicable to an objective eye refractive power measurement apparatus or a fundus camera that mounts a cornea shape measurement apparatus and an anterior segment cross-sectional image imaging apparatus.

While the invention has been illustrated and described in detail, the foregoing description is in all aspects illustrative and not restrictive. It is therefore understood that numerous modifications and variations can be devised without departing from the spirit and scope of the invention.

What is claimed is:

1. An ophthalmic apparatus comprising:
an infrared light source for irradiating an examinee's eye with infrared light;
an imaging optical system for imaging an anterior segment image including a pupil of the examinee's eye;
a computing part configured to detect an edge of the pupil by image processing from the anterior segment image irradiated with the infrared light obtained by the imaging optical system, and derive pupil information including a pupil diameter of the examinee's eye based on the detected result;
a memory part configured to store per multifocal intraocular lens size information of zones in a plurality of different multifocal intraocular lenses that have a far vision zone and a near vision zone; and
an output part for outputting the pupil information derived by the computing part and the size information stored in the memory part to be comparable.

2. The ophthalmic apparatus according to claim e including:
a monitor for displaying the anterior segment image obtained by the imaging optical system; wherein
the output part is configured to form a graphic that represents the far vision zone and the near vision zone based on the size information of the zones stored in the memory part, and display the graphic together with the pupil information of the examinee's eye on the monitor.

3. The ophthalmic apparatus according to claim 2, wherein
the output part is configured to form a first graphic corresponding to the pupil diameter derived by the computing part as the pupil information, form the graphic representing the far vision zone and the near vision zone as a second graphic, and display the first graphic and the second graphic on the monitor in a state where a center of the first graphic and a center of the second graphic correspond.

4. The ophthalmic apparatus according to claim 3, wherein
the memory part is configured to store product information for the plurality of multifocal intraocular lenses and the size information corresponding to the product information,
the apparatus further includes a selection part for selecting one product information from the plurality of product information stored in the memory part, and
the output part is configured to form the second graphic based on the size information corresponding to the product information selected by the selection part.

5. The ophthalmic apparatus according to claim 1 including:
a visible light source for irradiating the examinee's eye with visible light; wherein
the computing part is configured to detect the edge of the pupil by the image processing from the anterior segment image irradiated with the visible light obtained by the imaging optical system, and derive the pupil diameter of the examinee's eye in a bright-field state based on the detected result.

6. The ophthalmic apparatus according to claim 1 including:
a cornea shape detecting part for detecting a cornea shape based on a light receiving result of light reflected at a cornea of the examinee's eye; and
an anterior chamber depth detecting part for detecting an anterior chamber depth of the examinee's eye, wherein
the computing part is configured to derive an enlargement ratio, which is a ratio of an apparent anterior chamber depth to an actual anterior chamber depth, based on the detected results of the cornea shape detecting part and the anterior chamber depth detecting part, and derive the pupil diameter of the examinee's eye based on the detected result of the edge of the pupil detected by the image processing and the derived enlargement ratio.

7. The ophthalmic apparatus according to claim 6, wherein
the anterior chamber depth detecting part is configured to irradiate the examinee's eye with light or an ultrasound wave and detect the anterior chamber depth based on a light receiving result of the reflection light or a wave receiving result of the reflection wave.

8. The ophthalmic apparatus according to claim 6, wherein
the anterior chamber depth detecting part is configured to detect the actual anterior chamber depth of the examinee's eye by an optical interference type measuring unit utilizing an optical interference technique, and
the computing part is configured to derive the apparent anterior chamber depth based on the actual anterior chamber depth detected by the optical interference type measuring unit and the detected result of the cornea shape detecting part, and derive the enlargement ratio, which is the ratio of the apparent anterior chamber depth to the actual anterior chamber depth.

9. The ophthalmic apparatus according to claim 6, wherein
the anterior chamber depth detecting part is configured to have a light projecting optical system for projecting a slit light on the examinee's eye and a second imaging optical system for imaging an anterior segment cross-sectional image light-sectioned by the slit light based on a Scheimpflug principle, and detect the apparent anterior chamber depth based on the anterior segment cross-sectional image obtained by the second imaging optical system, and
the computing part is configured to derive the actual anterior chamber depth based on the apparent anterior chamber depth detected by the anterior chamber depth detecting part and the detected result of the cornea shape detecting part, and derive the enlargement ratio, which is the ratio of the apparent anterior chamber depth to the actual anterior chamber depth.

10. The ophthalmic apparatus according to claim 1, wherein
the output part is configured to display the anterior segment image obtained by the imaging optical system on the monitor as the pupil information.

11. An ophthalmic apparatus comprising:
a memory part for storing lens information that represents effective areas of a plurality of zones in a multifocal intraocular lens;
an imaging part for imaging an examinee's eye; and
a control part configured to derive a pupil size of the examinee's eye based on an image of the examinee's eye obtained by imaging, and output the pupil size together with the lens information.

12. The ophthalmic apparatus according to claim 11, wherein
the memory part is configured to store lens information of a plurality of different multifocal intraocular lenses, and
the control part is configured to output the pupil size and the lens information per multifocal intraocular lens.

13. The ophthalmic apparatus according to claim 12, including:
a monitor for displaying the image; wherein
the control part is configured to form a first graphic that represents a pupil profile and a second graphic that corresponds to an effective area of each zone in a state where a center of the first graphic and a center of the second graphic correspond.

14. The ophthalmic apparatus according to claim 13, wherein the control part is configured to derive the pupil size of the examinee's eye by eliminating influence by refraction at an interior of an eyeball and a cornea from the image of the examinee's eye.

15. The ophthalmic apparatus according to claim 14, wherein the control part is configured to derive an actual anterior chamber depth based on an apparent anterior chamber depth of the examinee's eye on the image of the examinee's eye and refraction indexes of the interior of the eyeball and the cornea, derive an enlargement ratio, which is a ratio of the apparent anterior chamber depth to the actual anterior chamber depth, and derive the pupil size of the examinee's eye by use of the enlargement ratio and the pupil size on the image of the examinee's eye.

\* \* \* \* \*